United States Patent [19]

Martin et al.

[11] Patent Number: 5,718,906
[45] Date of Patent: Feb. 17, 1998

[54] LIGHT-STABLE COSMETIC COMPOSITION

[75] Inventors: Roland Martin, Weinheim, Germany; Ralf Emmert, Goldens Bridge, N.Y.; Thekla Kurz, Gross-Zimmern, Germany; Gerd Bauer, Kleinostheim, Germany; Ulrich Heywang, Darmstadt, Germany

[73] Assignee: Merck Patent Gesellschaft Mit Beschrankter Haftung, Darmstadt, Germany

[21] Appl. No.: 408,295

[22] Filed: Mar. 22, 1995

[30] Foreign Application Priority Data

Mar. 23, 1994 [DE] Germany .................. 44 09 977.0

[51] Int. Cl.$^6$ .................................................. A61K 7/48
[52] U.S. Cl. ........................... 424/401; 424/59; 549/362
[58] Field of Search ............................ 424/401; 549/59, 549/362

[56] References Cited

U.S. PATENT DOCUMENTS 4,603,046  7/1986  Georgalas et al. .................. 424/59

OTHER PUBLICATIONS

Abstract of DE 3731831.
Abstract of JP 60-208908.
Journal of Natural Products, vol. 48, No. 1, Jan.–Feb. 1985, pp. 319–322.

*Primary Examiner*—Jyothsan Venkat
*Attorney, Agent, or Firm*—Millen, White, Zelano & Branigan, P.C.

[57]  ABSTRACT

A light-stable cosmetic composition for protection from UV rays having a wavelength of between 280 and 400 nm, which contains at least one tetraalkylquercetin in a cosmetically acceptable oil-based medium, and new tetraalkylquercetins.

15 Claims, No Drawings

LIGHT-STABLE COSMETIC COMPOSITION

The invention relates to a light-stable cosmetic composition for protection from UV rays having a wavelength of between 280 and 400 nm, which contains at least one tetraalkylquercetin in a cosmetically acceptable oil-based medium, and to new tetralkylquercetins.

BACKGROUND OF THE INVENTION

As is known, the skin reacts sensitively to solar rays, which can cause common sunburn or erythema, but can also burn to a greater or lesser degree.

However, solar rays also have other negative actions: they cause the skin to lose its elasticity and form wrinkles and thus lead to premature ageing. Dermatoses can also sometimes be observed. In the extreme case, skin cancer occurs in some people.

It is also desirable to protect hair against photochemical damage in order to prevent changes in color shades, decolorization or damage of a mechanical nature.

Further, it is known that the components contained in cosmetic preparations are not always sufficiently light-stable and decompose under the action of light rays.

As is known, the most dangerous part of solar rays is formed by the ultraviolet rays having a wave-length of less than 400 nm. It is also known that, due to the presence of the ozone layer of the earth's atmosphere, which absorbs some of the solar radiation, the lower limit of the ultraviolet rays which reach the earth's surface is about 280 nm.

It thus seems desirable to provide compounds which can absorb UV rays in a wavelength range from 280 to 400 nm, that is to say also UV-B rays having a wavelength of between 280 and 320 nm, which play a decisive role in the formation of solar erythema, and also UV-A rays having a wavelength of between 320 and 400 nm, which tan the skin but also cause it to age, promote the development of an erythematous reaction or magnify this reaction in certain people, or may even trigger phototoxic or photoallergic reactions.

The sunscreen filters now customary in cosmetics are classified into UVA and UVB filters. While there are good filters in the UVB range (280–320 nm) with substances such as Eusolex® 6300 or Eusolex® 232, those used in the UVA range (320–400 nm) present problems: dibenzoylmethanes, such as Parsol® 1789 or Eusolex® 8020 do not have an unlimited stability under UV irradiation, a fact which on the one hand reduces the effectiveness of the filter with time and on the other hand may promote photosensitization of the skin in individual cases. The benzophenones also used as UVA filters have only a limited solubility in the oils used in cosmetics, and they have a relatively low absorption.

German Patent Application DE 37 31 831 describes the use of tetrahydroxyethylrutin and of morpholinorutin as water-soluble light protection filters. JP 60 208908 claims the use of rutin and/or quercetin in the presence of further light protection filter substances. U.S. Pat. No. 4,603,046 relates to the use of tris(hydroxyalkyl) rutosides as water-soluble light protection filters.

Tetramethylquercetin was detected in flavonoids by R. P. Madhusudonan et al., J. Nat. Prod. 48 (2) 319–22, 1985.

SUMMARY OF THE INVENTION

An object of the present invention is to provide new light protection substances in oil-based sunscreen compositions.

Upon further study of the specification and appended claims, further objects and advantages of this invention will become apparent to those skilled in the art.

It has now been found that tetraalkylquercetins, i.e., quercetins alkylated on four of the hydroxy groups, have outstanding UVA filter properties. Their solubility in the oils used in cosmetics is good, so that concentrations of up to at least 10% are possible, even in complex formulations.

Particularly preferred are tetraalkylquercetins of the following formula

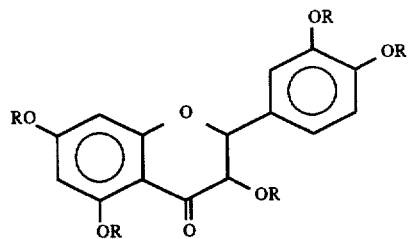

where four of the R groups are independently an alkyl group, preferably of 1–10 carbon atoms, and the fifth R group is hydrogen.

The compounds according to the invention furthermore have an exceptional photostability towards UV radiation, which by far exceeds the stability of UV filter substances known to date.

If the extinction in the UVB range has a minimum, this is not a disadvantage, since a UVB filter can be incorporated into the formulation without problems.

The compounds of the formula I can furthermore be used for the preventive treatment of inflammations and allergies of the skin and for prevention of certain types of cancer, such as those facilitated by exposure to UV rays.

In addition to their good properties as UV ray filters, the compounds according to the invention are distinguished by a good thermal and photochemical stability.

These compounds furthermore offer the advantage of not being toxic or irritating and of being completely harmless to the skin.

They disperse uniformly in the conventional cosmetic carriers and can form a continuous film, in particular in fatty carriers; they can be applied to the skin in this manner to form an effective protective film.

The invention thus relates to a light-stable cosmetic composition for protection from UV rays having a wavelength of between 280 and 400 nm, which contains at least one tetralkylquercetin in a cosmetically acceptable oil-based medium.

Particular preferred embodiments of the invention include the following:

a) Composition which contains 0.1 to 20 percent by weight of at least one tetraalkylquercetin.

b) Composition which contains at least one tetraalkyl quercetin and at least one other agent which absorbs UV rays, in particular wherein the other agents are UV-B filters which are chosen from salicylic acid esters, cinnamic acid esters, p-aminobenzoic acid esters, benzophenone derivatives, 3-benzylidenecamphor, 3-(4'-methylbenzylidene) camphor, 4-(2-oxo-3-bornylidenemethyl)-phenyltrimethylammonium-methyl acid, 2-methyl-5-(2-oxo-3-bornylidenemethyl)-benzenesulphonic acid, 2-phenylbenzimidazole-5-sulphonic acid, 3-benzylidene-2-oxo-10-bornanesulphonic acid, coffee oil and the metal or ammonium salts of these acids, or wherein the other agents are UV-A filters which are chosen from dibenzoylmethane derivatives, benzophenone derivatives and derivatives of benzene-1,4-[di(3- methylidene-camphor)] which are sulphonated on the methyl radical in the 10 position of the camphor, or wherein the other agents are inorganic UV filters which are chosen from titanium oxide and zinc oxide.

c) Cosmetic composition which furthermore comprises at least one cosmetic auxiliary chosen from lower monoalcohols or lower polyalcohols which contain 1 to 6 carbon atoms, mineral, animal, vegetable or synthetic oils and waxes, fatty acid esters, fatty alcohols, emulsifiers, thickening agents, hydrating products, alleviating agents, dyestuffs, opacifying agents, preservatives, perfumes, agents for regulating the pH and propellants.

d) Cosmetic composition which has a pH of from 4 to 9, preferably from 5.5 to 8.

e) Cosmetic composition which is in the form of a lotion, emulsion, pomade, gel or aerosol.

f) Cosmetic composition for application to the hair, which is in the form of a shampooing agent, a lotion, a gel or an emulsion for rinsing, a styling or treatment lotion or a corresponding gel, a lotion or a gel for blow-drying or for setting the hair, as a hair lacquer, as a permanent wave composition or as a composition for decolorizing or dyeing.

g) Composition which furthermore contains at least one cosmetic auxiliary chosen from surface-active agents, thickening agents, polymers, alleviating agents, preservatives, foam stabilizers, electrolytes, organic solvents, siliconized derivatives, oils, waxes, antigrease agents, dyestuffs and pigments.

h) Composition which is in the form of a dyed or non-dyed cosmetic formulation and is stabilized towards light, characterized in that it is a hair composition or a make-up product which contains 0.1 to 10 % by weight of at least one tetraalkyquercetin.

The invention furthermore relates to a method for protecting the skin and hair from sunlight, characterized in that an adequate amount of a cosmetic composition which contains at least one tetraalkylquercetin according to claim 1 is applied to the skin or hair.

The invention furthermore relates to tetraalkylquercetins of the formula I

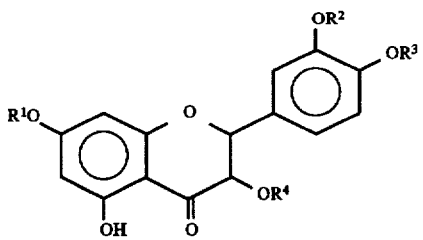

wherein $R^1$, $R^2$, $R^3$ and $R^4$ in each case independently of one another are $C_{1-10}$-alkyl, of branched or straight chain, with the proviso that tetramethylquercetin is excluded.

Preferred compounds of the formula I are those wherein the radicals $R^1$ to $R^4$ are identical and are $C_{2-8}$-alkyl, in particular wherein these radicals are ethyl, 1-propyl, n-butyl, n-pentyl, n-hexyl, n-heptyl, n-octyl or 2-ethyl-hexyl.

The invention also relates to the process for the preparation of the compounds of the formula I.

The compounds of the formula I are obtained, for example, by reacting quercetin with a halogenoalkane or a dialkyl sulphate in the presence of a base.

The reaction is as a rule carried out in an inert solvent, preferably a polar, aprotic solvent, such as, for example, dimethylformamide (DMF), N-methyl-pyrrolidinone (NMP) or dimethyl sulfoxide (DMSO). Preferably, 4 to 10 mol, in particular 6 to 9 mol, of alkylating agent are employed per 1 mol of quercetin. If chloro- and bromoalkanes are used as alkylating agents, it has proved advantageous to add less than the stoichiometric amounts of iodides, preferably alkali metal iodides, in particular potassium iodide.

The invention furthermore relates to a cosmetic formulation which contains an effective amount of at least one compound of the, above formula I in a cosmetically tolerated carrier.

The cosmetic composition according to the invention can be used as a composition for protection of the human epidermis or the hair or as a sunscreen composition.

The invention furthermore relates to a method for protecting the skin and natural or sensitized hair from solar rays, wherein an effective amount of at least one compound of the formula I is applied to the skin or hair.

By "sensitized hair" is meant hair which has been subjected to a permanent wave treatment or a dyeing or decolorizing process.

The invention furthermore relates to a dyed or non-dyed light-stabilized cosmetic formulation which comprises an effective amount, e.g., UV-ray protecting amount, of at least one tetraalkylquercetin of the above formula I.

If the cosmetic composition according to the invention is used as a composition for protecting the human epidermis against UV rays, it may be in the various forms usually used for this type. It can thus be, in particular, in the form of oily or oily-alcoholic lotions, emulsions, such as a cream or milk, in the form of oily-alcoholic, oily-aqueous or aqueous-alcoholic gels or as solid sticks, or can be made up as an aerosol. It may contain cosmetic adjuvants which are usually used in this type of composition, such as, for example, thickening agents, softening agents, humidifying agents, surface-active agents, preservatives, agents against foam formation, perfumes, waxes, lanolin, propellants, dyestuffs and/or pigments which color the composition itself or the skin, and other ingredients usually used in cosmetics.

The compound of the formula I is preferably contained in an amount of 0.1 to 10% by weight, particularly preferably 0.3 to 6% by weight, based on the total weight of the cosmetic composition for protection of the human epidermis.

An oil, wax or other fatty substance, a lower monoalcohol or a lower polyol or mixtures thereof can be used as solubilizing agents. The particularly preferred monoalcohols or polyols include ethanol, i-propanol, propylene glycol, glycerol and sorbitol.

A preferred embodiment of the invention is an emulsion which is in the form of a protective cream or milk, and in addition to the compound of the formula I comprises fatty alcohols, fatty acid esters, in particular triglycerides of fatty acids, fatty acids, lanolin, naturally occurring or synthetic oils or emulsifiers in the presence of water.

Other preferred embodiments are oily lotions based on naturally occurring or synthetic oils and waxes, lanolin, fatty acid esters, in particular triglycerides of fatty acids, or oily-alcoholic lotions based on a lower alcohol, such as ethanol, or on a glycol, such as propylene glycol, and/or on a polyol, such as glycerol, and oils, waxes and fatty acid esters, such as triglycerides of fatty acids.

The cosmetic composition according to the invention can also be in the form of an alcoholic gel which comprises one or more lower alcohols or lower polyols, such as ethanol, propylene glycol or glycerol, and a thickening agent, such as silica. The oily-alcoholic gels may furthermore contain naturally occurring or synthetic oils or waxes.

The solid sticks comprise naturally occurring or synthetic waxes and oils, fatty alcohols, fatty acids, lanolin and other fatty substances.

The invention also relates to cosmetic sunscreen compositions which contain at least one compound of the formula I and can include other UVB and/or UVA filters.

In this case, the amount of filter of the formula I is preferably from 0.2 to 8.0% by weight, particularly preferably from 0.4 to 5.0% by weight, based on the total weight of the sunscreen composition.

If a composition is made up as an aerosol, the customary propellants, such as alkanes, fluoroalkanes and chlorofluoroalkanes, are preferably used.

If the composition according to the invention is to protect natural or sensitized hair from UV rays, it can be in the form of a shampoo, lotion, gel or emulsion for rinsing out, the particular formulation being applied before or after shampooing, before or after dyeing or decolorizing or before or after a permanent wave; or the composition is in the form of a lotion or gel for styling and treatment, as a lotion or gel for brushing or setting a water wave, as a hair lacquer, permanent wave composition or dyeing or decolorizing composition for hair. In addition to the compound according to the invention, this composition can contain various adjuvants used in this type of composition, such as surface-active agents, thickening agents, polymers, softening agents, preservatives, foam stabilizers, electrolytes, organic solvents, silicone derivatives, oils, waxes, anti-grease agents, dyestuffs and/or pigments which dye the composition itself or the hair, or other ingredients usually used for hair care. The composition preferably contains 0.3 to 5.0% by weight of the compound of the formula I.

The present invention also relates to cosmetic compositions which contain at least one compound of the formula I being an agent for protection against UV rays and also being an antioxidant. These compositions include hair products, such as hair lacquers, water wave lotions for setting the hair, if appropriate for treatment or lighter styling, shampoos, color shampoos, hair dyeing compositions, decorative products, such as nail varnish, creams and oils for skin treatment, make-up (foundation), lipsticks, skin care compositions, such as bath oils or creams, and other cosmetic compositions which may present problems with light stability and/or oxidation in the course of storage in view of their components. Such compositions preferably contain 0.3 to 5.0% by weight of a compound of the formula I.

The invention furthermore relates to a process for protecting the cosmetic compositions from UV rays and oxidation, wherein an effective amount of at least one compound of the formula I is added to these compositions.

The invention furthermore relates to the use of the compounds of the formula I as solar filters having a wide absorption breadth in a wavelength range from 280 to 400 nm.

The invention furthermore relates to the use of the compounds of the formula I as cosmetic products.

The invention furthermore relates to a pharmaceutical composition which contains an effective amount of at least one compound of the formula I as an active compound in a non-toxic carrier or excipient.

The pharmaceutical compositions according to the invention can be administered orally or topically for the above-stated uses.

For oral administration, the pharmaceutical composition is in the form of pastilles, gelatin capsules or coated tablets or as a syrup, suspension, solution, emulsion and the like. For topical administration, it is in the form of an ointment, cream, pomade, solution, lotion, gel, spray, suspension and the like.

This composition can contain inert or pharmacodynamically active additives, in particular hydrating agents, antibiotics, steroidal or non-steroidal antiinflammatory agents, carotinoids and agents against psoriasis.

This composition can also contain flavor-improving agents, preservatives, stabilizers, moisture regulators, pH regulators, modifiers for osmotic pressure, emulsifiers, local anaesthetic, buffers and the like.

It can furthermore be made up in a manner known, per se, in sustained release form or in a form in which the active compound is released rapidly.

The following examples are representative of the present invention.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 09 977.0, filed Mar. 23, 1994, are hereby incorporated by reference.

EXAMPLES

The extinctions are determined at the stated wavelength in a path length of 1 cm.

Example 1

2-(3,4-Diethoxyphenyl)-2,3-dihydro-5-hydroxy-3,7-diethoxy-4H-1-benzopyranone (tetraethylquercetin)

123.3 g of bromoethane are added to a mixture of 40 g of quercetin, 400 ml of dimethylformamide, 4.0 g of potassium iodide and 200 g of potassium carbonate at 50° C. in the course of 1 hour.

After the mixture has been stirred at 50° C. for 2 hours, 300 ml of water are added and the solid constituents are separated off and washed with water. The residue is recrystallized from 150 ml of toluene. After drying, 11.6 g of the product are obtained in the form of yellow-orange crystals.

The spectra correspond to the expected UV compound (i-propanol, c=1 mg/100 ml): $\lambda_{max}$=354 nm, E=0.54.

The following are prepared analogously:

| Tetraalkylquercetin | $\lambda_{max}$ | E | Solvent |
| --- | --- | --- | --- |
| Tetrapropylquercetin | 352 | 0.45 | i-propanol |
| Tetrabutylquercetin | 348 | 0.32 | heptane |
| Tetraisobutylquercetin | 348 | 0.38 | heptane |
| Tetrapentylquercetin | 348 | 0.32 | heptane |
| Tetrahexylquercetin | 348 | 0.34 | heptane |
| Tetraheptylquercetin | 341 | 0.28 | heptane |
| Tetraoctylquercetin | 348 | 0.25 | heptane |
| Tetra(2-ethylhexyl)quercetin | 350 | 0.30 | heptane |

Example 2

Sunscreen cream (W/O)

| | | | % |
| --- | --- | --- | --- |
| A | Tetraoctylquercetin | (1) | 0.20 |
| | Arlacel 581 | (2) | 6.00 |
| | Paraffin oil, viscous (Art. No. 7160) | (1) | 17.50 |
| | Beeswax, bleached (Art. No. 11544) | (1) | 3.00 |

-continued

|   |   |   | % |
|---|---|---|---|
|   | Miglyol 812 | (3) | 11.50 |
|   | Dow Corning 200 (100 cs) | (4) | 2.00 |
|   | Tocopherol acetate (Art. No. 500952) | (1) | 0.50 |
| B | Glycerol (Art. No. 4093) | (1) | 2.00 |
|   | Magnesium sulphate heptahydrate (Art. No. 5882) | (1) | 0.70 |
|   | Preservative |   | q.s. |
|   | Water, demineralized |   | to 100.0 |

Preparation:

Heat phase A to 75° C. and phase B to 80° C. Stir phase B slowly into phase A. Homogenize. Cool, while stirring. If appropriate, perfume at 40° C.

Sources of supply:

(1) E. Merck, Darmstadt
(2) ICI, Essen
(3) Hüls Troisdorf AG, Witten
(4) Dow Corning, Düsseldorf Example 3

Sunscreen milk (W/O)

|   |   |   | % |
|---|---|---|---|
| A | Tetraoctylqueraetin | (1) | 0.20 |
|   | Abil WE 09 | (2) | 5.00 |
|   | paraffin oil, highly liquid (Art. No. 7174) | (1) | 35.00 |
|   | Paraffin wax |   | 3.00 |
|   | Water, demineralized |   | to 100.0 |

Preparation:

The components of phase A are admixed and heated to 75° C., while stirring, then cooled, while stirring, and, if appropriate, perfume is added at 40° C.

Sources of supply:

(1) E. Merck, Darmstadt
(2) Th. Goldschmidt, Essen

Comparison Example

A sunscreen milk is prepared according to Example 3, tetraoctylquercetin being replaced by Eusolex 8020.

In each case 1 mg of the sunscreen compositions thus obtained is dissolved in 100 ml of heptane, the solution is exposed to a UV lamp (Vitalux) at a distance of 50 cm, while cooling, in a path length of 250 μm and the extinction is then determined.

The results of this stability test can be seen from Table 1:

TABLE 1

| Substance | Extinction before exposure | Extinction after exposure | Decomposition |
|---|---|---|---|
| Comparison example | 1.07 | 0.4 | about 60% |
| Example 3 | 0.28 | 0.26 | about 7% |

Example 4

Sunscreen cream

|   |   |   | % |
|---|---|---|---|
| A | Tetraoctylquercetin | (1) | 1.00 |
|   | Emulgade 1000 Ni |   | 10.00 |
|   | Paraffin oil, viscous (Art. No. 7160) | (1) | 2.00 |
|   | Dow Corning 200 (100 cs) | (2) | 0.50 |
| B | Glycerol | (1) | 5.00 |
|   | EDTA | (1) | 5.00 |
|   | Water |   | to 100.0 |

Preparation

Heat phase A to 75° C. and phase B to 80° C. Stir phase A into phase B. Homogenize.

Sources of supply:

(1) E. Merck, Darmstadt
(2) Dow Corning, Düsseldorf

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A light-stable cosmetic composition for protection from UV rays having a wavelength of between 280 and 400 nm, comprising at least one tetraalkylquercetin in a cosmetically acceptable oil-based medium.

2. A composition according to claim 1, comprising 0.1 to 20 percent by weight of at least one tetraalkylquercetin.

3. A composition according to claim 1, comprising at least one tetraalkylquercetin and at least one other agent which absorbs UV rays.

4. A cosmetic composition according to claim 3, wherein the at least one other agent which absorbs UV rays is a UV-B filter selected from the group consisting of salicylic acid esters, cinnamic acid esters, p-aminobenzoic acid esters, 3-benzylidenecamphor, 3-(4'-methylbenzyl-idene) camphor, 4-(2-oxo-3-bornylidenemethyl)phenyltrimethylammoniummethyl acid, 2-methyl-5-(2-oxo-3-bornylidenemethyl)-benzenesulphonic acid, 2-phenyl-benzimidazole-5-sulphonic acid, 3-benzylidene-2-oxo-10-bornanesulphonic acid, coffee oil and the metal and ammonium salts of these acids.

5. A cosmetic composition according to claim 3, wherein the at least one other agent which absorbs UV rays is the UV-A filter benzene-1,4-[di(3-methylidene-camphor)] which is sulphonated on the methyl radical in the 10-position of the camphor.

6. A cosmetic composition according to claim 3, wherein the at least one other agent which absorbs UV rays is an inorganic UV filter selected from the group consisting of titanium dioxide and zinc oxide.

7. A cosmetic composition according to claim 1, for application to the skin, further comprising at least one cosmetic auxiliary selected from the group consisting of lower monoalcohols or lower polyalcohols which contain 1 to 6 carbon atoms, mineral, animal, vegetable or synthetic oils and waxes, fatty acid esters, fatty alcohols, emulsifiers, thickening agents, hydrating products, alleviating agents, dyestuffs, opacifying agents, preservatives, perfumes, agents for regulating the pH and propellants.

8. A cosmetic composition according to claim 7 having a pH of 4 to 9.

9. A cosmetic composition according to claim 7, having a pH of 5.5 to 8.0.

10. A cosmetic composition according to claim 1, wherein the composition is in the form of a lotion, emulsion, pomade, gel or aerosol.

11. A cosmetic composition according to claim 1 for application to the hair, which is in the form of a shampooing agent, a lotion, a gel or an emulsion for rinsing, a styling or treatment lotion or a corresponding gel, a lotion or a gel for blow-drying or for setting the hair, a hair lacquer, a permanent wave composition or a composition for decolorizing or dyeing.

12. A cosmetic composition according to claim 11, comprising at least one cosmetic auxiliary chosen from surface-active agents, thickening agents, polymers, alleviating agents, preservatives, foam stabilizers, electrolytes, organic solvents, siliconized derivatives, oils, waxes, anti-grease agents, dyestuffs and pigments.

13. A cosmetic composition according to claim 1 in the form of a dyed or non-dyed cosmetic formulation which is stabilized towards light, being a hair composition or a make-up product which contains 0.1 to 10% by weight of at least one tetraaklylquercetin.

14. A cosmetic composition according to claim 1, wherein the tetraalkylquercetin is of the following formula:

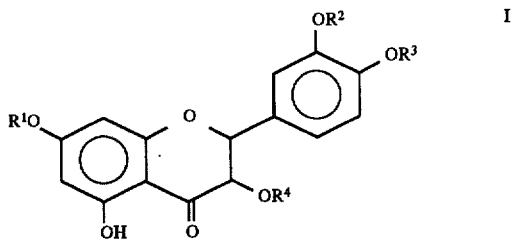

wherein $R^1$, $R^2$, $R^3$ and $R^4$ are each independently an alkyl group of 1–10 carbon atoms.

15. A method for protecting the skin and hair against solar light, comprising applying a UV-ray protecting effective amount of a cosmetic composition which contains at least one tetraalkylquercetin according to claim 1 to the skin or hair.

* * * * *